United States Patent
Sanada et al.

(10) Patent No.: US 7,102,030 B2
(45) Date of Patent: Sep. 5, 2006

(54) METHOD FOR MANAGING OPERATION OF GAS PHASE REACTION APPARATUS

(75) Inventors: Kenji Sanada, Himeji (JP); Yukihiro Matsumoto, Kobe (JP); Takeshi Nishimura, Himeji (JP); Harunori Hirao, Himeji (JP)

(73) Assignee: Nippon Shokubai, Co., LTD, Osaka (JP)

( * ) Notice: Subject to any disclaimer, the term of this patent is extended or adjusted under 35 U.S.C. 154(b) by 14 days.

(21) Appl. No.: 10/796,254

(22) Filed: Mar. 9, 2004

(65) Prior Publication Data

US 2004/0181090 A1      Sep. 16, 2004

(30) Foreign Application Priority Data

Mar. 14, 2003 (JP) ............................. 2003-070786

(51) Int. Cl.
*C07C 51/16* (2006.01)
(52) U.S. Cl. ...................................... 562/545; 562/547
(58) Field of Classification Search .................... None
See application file for complete search history.

(56) References Cited

FOREIGN PATENT DOCUMENTS

| | | | |
|---|---|---|---|
| EP | 1 080 780 A1 | 8/2000 | |
| JP | 2001-114706 | * | 4/2001 |
| JP | 2001-120984 | | 5/2001 |
| JP | 2001-122805 | | 5/2001 |
| JP | 2001-137688 | | 5/2001 |
| JP | 2001-137689 | | 5/2001 |

* cited by examiner

*Primary Examiner*—Paul A. Zucker
(74) *Attorney, Agent, or Firm*—Mathews, Shepherd, McKay & Bruneau, P.A.

(57) ABSTRACT

A method for managing the operation of an apparatus for the reaction of gas phase partial oxidation of an unsaturated hydrocarbon with a molecular oxygen-containing gas for the purpose of omitting wasteful emergency stop of the operation and ensuring execution of necessary emergency measure and a method for producing (meth) acrylic acid by utilizing the method mentioned above are provided. The operation of the apparatus is brought to emergency stop exclusively when thee values of concentrations of various gases obtained by calculation from the flow rates of the gases being introduced at the inlet port of the reactor and the measured values obtained by analysis with gas analyzing instruments both deviate from the ranges of the present values.

7 Claims, 3 Drawing Sheets

METHOD FOR MANAGING OPERATION OF GAS PHASE REACTION APPARATUS

BACKGROUND OF THE INVENTION

1. Field of the Invention

This invention relates to a method for managing the operation of an apparatus for the reaction of gas phase partial oxidation of an unsaturated hydrocarbon with a molecular oxygen-containing gas and to a method for the production of (meth)acrylic acid. More particularly, it relates to a method for managing the operation of an apparatus for the reaction of gas phase oxidation such as for the production of acrylic acid or acrolein by the gas phase partial oxidation of propylene with a molecular oxygen-containing gas, the production of methacrylic acid or methacrolein by the gas phase partial oxidation of isobutylene, and the production of ethylene oxide by the gas phase partial oxidation of ethylene and a method for the production of (meth)acrylic acid.

2. Description of the Related Art

Since such oxidizable raw materials as propylene, isobutylene, and ethylene are generally formed an explosive mixture by being mixed with molecular oxygen, the flow rate of such a raw material and the flow rate of a molecular oxygen-containing gas are so set that the composition of the raw material gas may normally avoid entering the inflammable area.

The management of the composition of a raw material gas, therefore, is executed by controlling the flow rate of each of the gases at a set value. Since this method of management possibly suffers the composition of the gas to fall within the inflammable area when such a measuring instrument as a flow meter encounters abnormality, it requires the composition of the gas to be detected by a proper method.

As a way of detecting the composition of a raw material gas, the analysis by means of various online analyzing instruments generally prevails. In the case of the conventional device for the reaction of gas phase oxidation, when the value of the composition of a raw material gas measured by the analysis deviates from the preset range, this device is at once brought to emergency stop automatically as by a process control device, for example. Conceivably, the preset values of various flow rates may be automatically controlled by the indications on analyzing instruments (refer to the official gazette of JP-A-2001-122805, the official gazette of JP-A-2001-114706, and the official gazette of JP-A-2001-120984, for example).

In the case of such a device, however, even when the value of the composition of a raw material gas actually measured happens to represent a deviation from the range of preset value, it is not necessarily improbable that this deviation originates in an erroneous operation of the device. The stop of the operation of the device in response to this deviation inevitably jeopardizes the economy of the operation itself.

It is, therefore, an object of this invention to provide a novel method for managing the operation of an apparatus for the reaction of gas phase oxidation.

Another object of this invention is to provide a novel method for managing the operation of an apparatus for the reaction of gas phase oxidation which excels in safety and economy.

SUMMARY OF THE INVENTION

The objects mentioned above are accomplished by the following items (1)–(6).

(1) A method for managing the operation of an apparatus for the reaction of gas phase oxidation while the apparatus is in trouble, characterized by stopping the operation of the apparatus exclusively when the value of the concentration of a gas obtained by calculation based on the flow rate of the gas at the inlet port of the relevant reactor and the value measured by analysis with a gas analyzing instrument both deviate from the relevant preset ranges.

(2) A method set forth in the preceding item (1), wherein the stop of the operation mentioned above is effected by causing the concentration of a raw material gas and the concentration of oxygen at the inlet port of the reaction vessel to be automatically calculated by an inlet gas concentration calculating device on the basis of the material balance using the measured values of flow rate, pressure and temperature at various points, and the fixed input values depended on the operation conditions and causing the consequently calculated concentrations to be rated with the object of determining whether or not they fall in the range between the upper limit values and the lower limit values of the preset concentrations.

(3) A method set forth in the preceding item (1) or (2), wherein the raw materials supplied to the reaction device are an unsaturated hydrocarbon and a molecular oxygen-containing gas.

(4) A method set forth in any of the preceding items (1)–(3), wherein the unreacted hydrocarbon is an unsaturated hydrocarbon of 2–4 carbon atoms.

(5) A method set forth in any of the preceding items (1)–(4), wherein the unsaturated hydrocarbon is propylene or isobutylene.

(6) A method for the production of (meth)acrylic acid by the gas phase oxidation of an unsaturated hydrocarbon with a molecular oxygen-containing gas in accordance with a method for managing the operation set forth in either of the preceding items (1) and (2).

The method for managing the operation of an apparatus for the reaction of gas phase oxidation contemplated by this invention is characterized, as described above, by stopping the operation of the apparatus exclusively when the values of the concentrations of the relevant gases obtained by calculation based on the flow rates of the gases being introduced and the values measured by a gas analyzing instrument both deviate from the relevant preset ranges. Thus, this method as compared with the conventional method which brings the operation of the apparatus to emergency stop even when either of the values deviates from the preset range, is at an advantage in veritably minimizing the economic loss due to the stop of operation plus infallibly bringing the operation to a stop at the time of actual trouble.

DESCRIPTION OF THE PREFERRED EMBODIMENT

The term "unsaturated hydrocarbon" as used in this invention refers to an unsaturated hydrocarbon having 2–4 carbon atoms. As typical examples of the unsaturated hydrocarbon, ethylene, propylene, n- and isobutylene, 1,3-butadiene, etc. may be cited. Owing to the gas phase partial oxidation with a molecular oxygen-containing gas, these unsaturated hydrocarbons form their corresponding oxides. For example, propylene produces acrylic acid and acrolein by partial oxidation, isobutylene produce methacrylic acid and methacrolein by partial oxidation, ethylene produces ethylene oxide by partial oxidation, and 1,3-butadiene produces 3,4-epoxy-1-butene by partial oxidation. Among other productions enumerated above, the production of acrylic acid and acrolein by the partial oxidation of propylene and the production of methacrylic acid and methacrolein by the partial oxidation of isobutylene prove particularly advantageous.

Now, the mode of embodying this invention will be described below with reference to the accompanying drawing.

Figure 1:
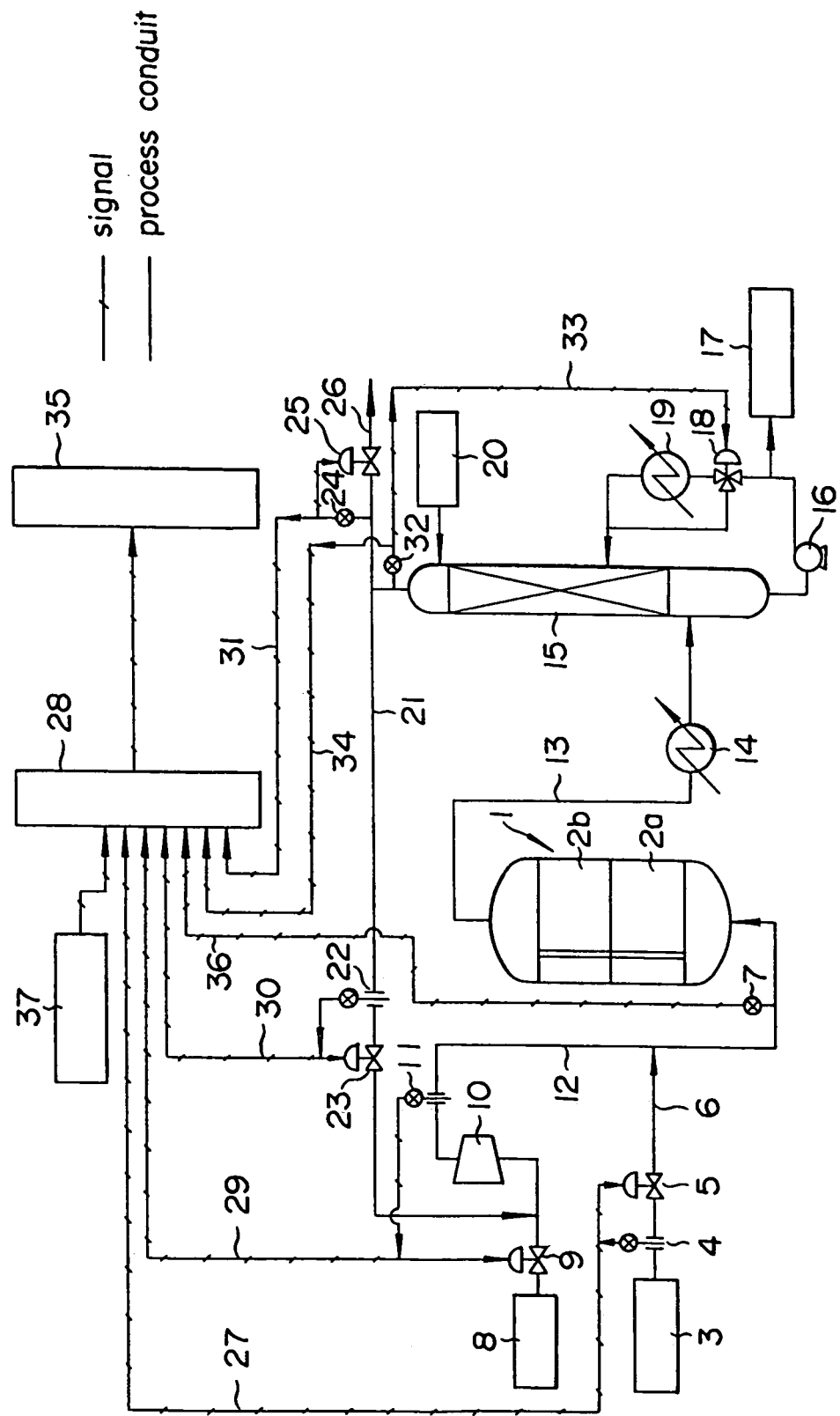
FIG. 1 is a flow sheet illustrating one preferred mode of embodying the method of this invention for managing the operation of an apparatus for the gas phase reaction.

One example of the production of acrylic acid by the partial oxidation of propylene is illustrated in FIG. 1.

In a process for performing a step of forming acrolein by the oxidation of propylene and a step of forming acrylic acid by the oxidation of acrolein both in a single reactor 1 as illustrated in FIG. 1 thereby producing acrylic acid by the catalytic gas phase oxidation of propylene, a former stage side region 2a of the reactor 1 is packed with a former stage catalyst for the formation of acrolein and a latter stage side region 2b of the reactor 1 is packed with a latter stage catalyst for the formation of acrylic acid.

Subsequently, a raw material is supplied from a source 3 of propylene supply through a flow meter 4 and a control value 5 and via a conduit 6 to the former stage side region 2a of the reactor 1 and air is supplied from a source 8 of air supply through a control valve 9, a blower 10, and a flow meter 11 and via a conduit 12 to the former stage side region 2a of the reactor 1.

The reaction product gas discharged from the latter stage side region 2b of the reactor 1 is advanced by a conduit 13 and introduced via a heat exchanger 14 to the lower part of an absorption column 15. The reaction product gas which has made counterflow contact with an absorption liquid 20 supplied from above in the absorption column 15 and consequently has such reaction products as acrylic acid absorbed by the absorption liquid is recovered as a collected liquid via a pump 16 from the bottom of the column. Further, part of this collected liquid is advanced through a control valve 18 and a heat exchanger 19 and returned to the medium stage of the absorption column 15. Such gases as the unreacted propylene and nitrogen gas are separated through the top of the column and partly recycled through a conduit 21 to the reactor 1 via a flow meter 22 and a control valve 23. The remaining gases are advanced via a pressure gauge 24 and a control valve 25 and discharged through a conduit 26.

The measured value of the propylene 3 indicated on the flow meter 4 is transmitted as a single by a wire 27 to an inlet gas concentration calculating device 28. The measured value of air 8 indicated on the flow meter 11 is transmitted as a signal by a wire 29 to the inlet gas concentration calculating device 28. The measured values of the recycling gas indicated on the control valve 23 and the flow meter 22 are also transmitted as signals by a wire 30 to the inlet gas concentration calculating device 28. Further, the measured value of the discharged gas 26 indicated on the pressure gauge 24 is transmitted as a signal by a wire 31 to the inlet gas concentration calculating device 28. The measured value of the top of the absorption column 15 indicated on a thermometer 32 is transmitted as a signal by a wire 33 to the control valve 18 and enabled therein to control the degree of opening thereof and control the amount of a material passed through the heat exchanger 19 as well and further transmitted as a signal by a wire 34 to the inlet gas concentration calculating device 28.

Then, the propylene concentration and the oxygen concentration at the inlet port of the reactor 1 are automatically calculated by the inlet gas concentration calculating device 28 which serves as a process control device on the basis of the material balance using the measured values of the flow rate of propylene as the raw material, the flow rate of air, the flow rate of the recycling as from the top of the absorption column, the temperature of the top of the column, and the pressure in the top of the column obtained by the use of the flow meters, thermometer, and pressure gauge and the fixed input values 37 of the air temperature, humidity, degree of conversion of propylene, and purity of propylene. The concentrations consequently found by the automatic calculation are rated with the object of determining whether or not they fall in the ranges between the upper limit values and the lower limit values of the relevant concentrations.

Meanwhile, the concentration of propylene at the inlet port of the reactor 1 is assayed with a gas concentration analyzing instrument 7 resorting to the principle of gas chromatography. The measured value of this concentration is transmitted as a signal by a wire 36 to the inlet gas concentration calculating device 28, in which the value is rated with the object of determining whether or not it falls in the range between the upper limit value and the lower limit value of the relevant concentration.

Figure 2:
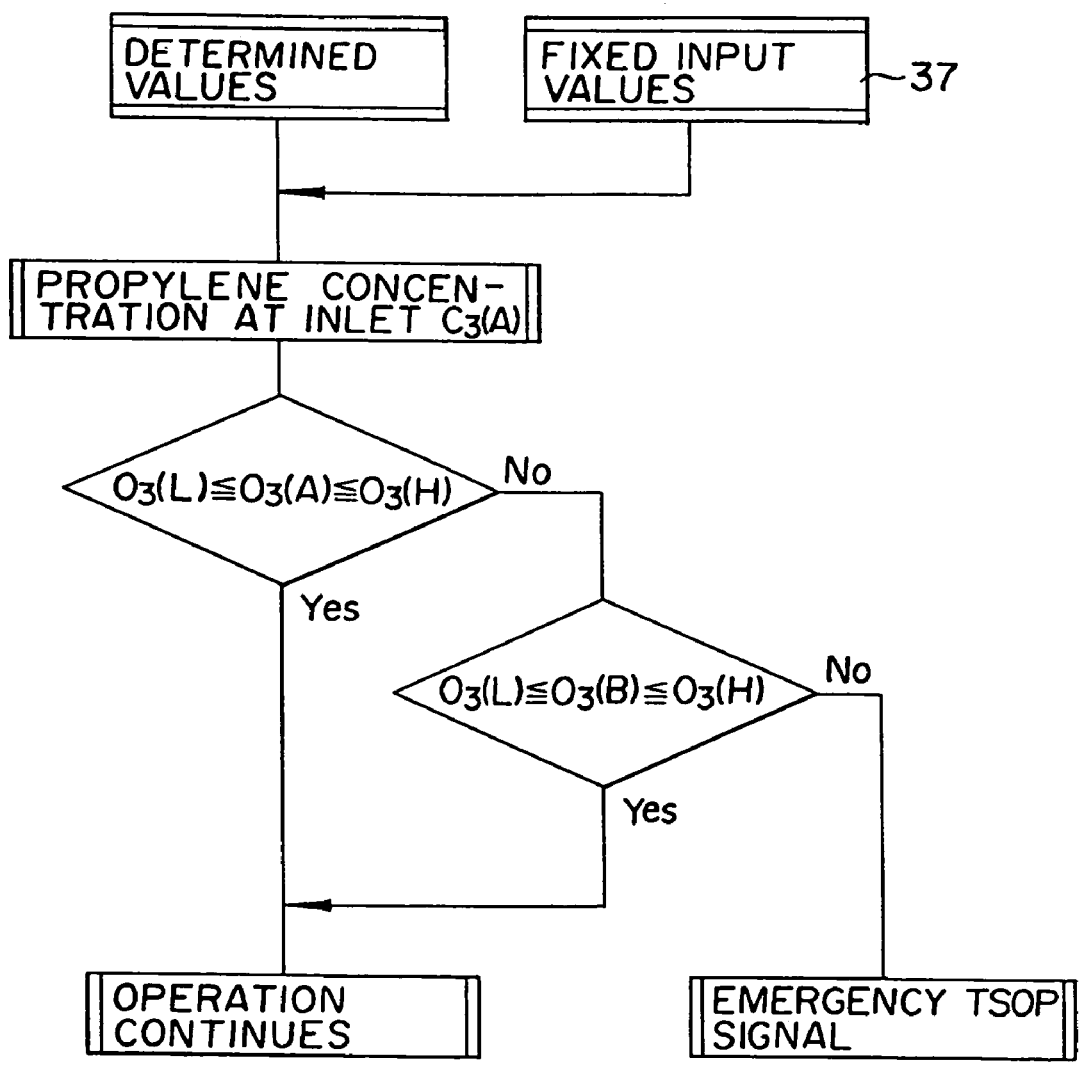
FIG. 2 is a flow sheet illustrating a mechanism for emergency stop in the apparatus for the gas phase reaction contemplated by this invention.

Specifically, the propylene concentration in the inlet gas is calculated on the basis of the fixed inlet values 37 and the measured values indicated on the various flow meters, thermometers, and pressure gauges as illustrated in FIG. 2. Let $C_3$ (A) stand for the propylene concentration consequently found by the calculation.

The propylene concentration in the inlet gas which is measured with the gas concentration analyzing instrument 7 is denoted as $C_3$ (B). The upper limit value and the lower limit value of the propylene concentration during the course of reaction are denoted respectively as $C_3$ (H) and $C_3$ (L).

The apparatus constructed as described above continues its operation while the propylene concentration $C_3$ (A) automatically calculated by the instruments remains in the range between these preset values, $C_3$ (L) and $C_3$ (H).

Then, in the case of the deviation of the propylene concentration $C_3$ (A) from the limits of the preset values, the operation is continued while the propylene concentration $C_3$ (B) which is a measured value obtained by the analysis with the gas concentration analyzing instrument remains between the preset values $C_3$ (L) and $C_3$ (H), whereas the operation is brought to emergency stop when the signal from the inlet gas concentration calculating device 28 is sent to a reactor emergency stop device 35 with the object of actuating this device.

Though the mode of embodying this invention has been described with reference to the concentration of propylene, for example, this invention can be similarly embodied with reference to the concentration of oxygen. These modes may be executed either singly or jointly.

Generally the online analyzing instruments are not directly disposed in the process piping and the samples are more often than not supplied via sampling conduits to the online analyzing instruments. In the apparatus for the production of such an easily polymerizing substance as acrylic acid, the substance forms a polymer in the piping of this sort and eventually blocks this piping and constitutes a cause for erroneous operation of the analyzing instruments. Further, the analyzing instruments are things rich in precision as compared with such things as flow meters and some of them incorporate mechanically operating parts. They, they have higher possibility of inducing an erroneous operation.

Further, the possibility of the embodiment requiring installation of a plurality of analyzing instruments is not deniable. When one of these instruments happens to develop an erroneous operation, however, this embodiment does not allow due judgment as to which of the instruments is accurate. Even in this case, the reference to the calculated values allows judgment as to which of the instruments is accurate and results in exalting the accuracy of judgment as to whether an emergency stop is necessary or not.

Figure 3:
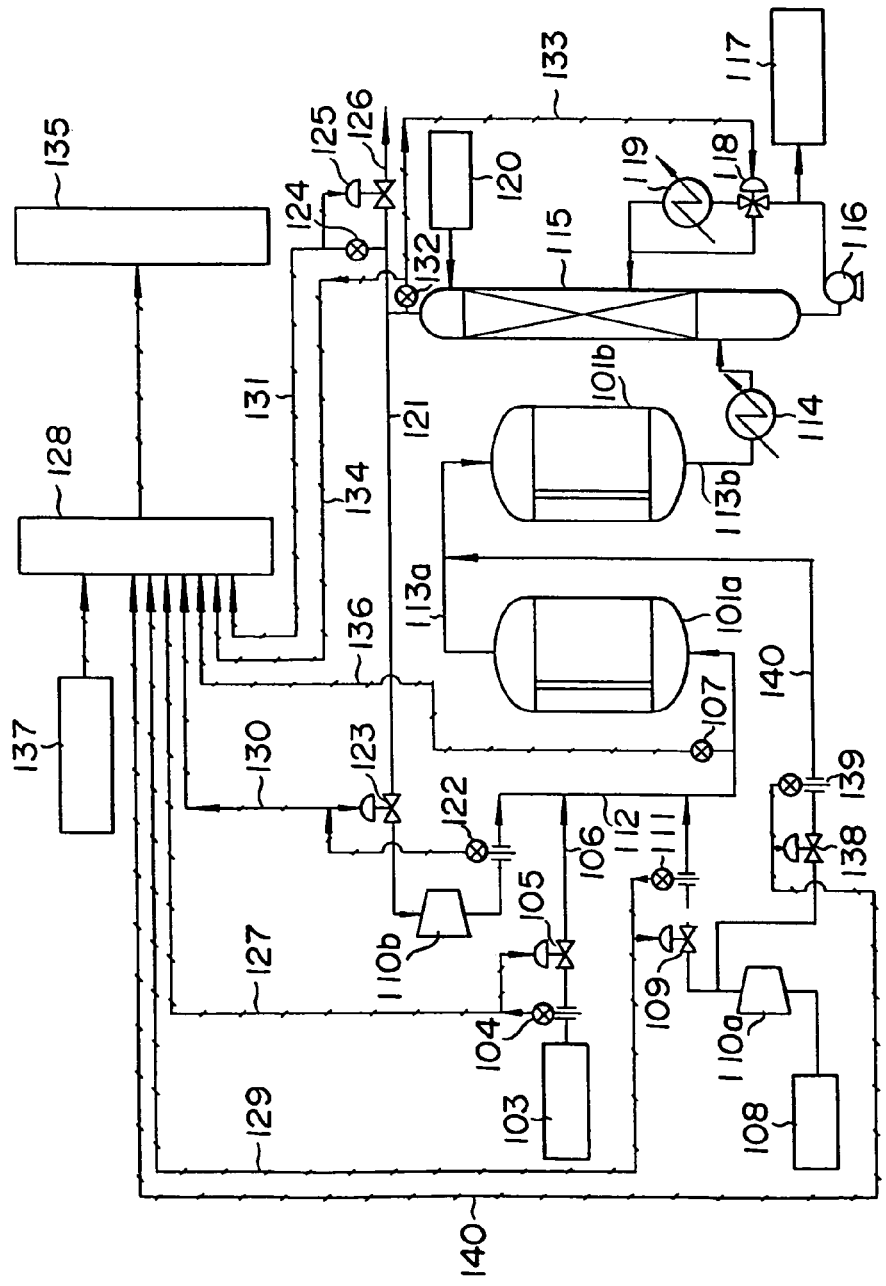
FIG. 3 is a flow sheet illustrating another preferred mode of embodying the method of this invention for managing the operation of an apparatus for the gas phase reaction.

FIG. 3 illustrates another mode of embodying this invention. This embodiment concerns a process for the production of acrylic acid by the use of a former stage reactor 101a for forming acrolein mainly by the oxidation of propylene and a latter stage reactor 101b for forming acrylic acid mainly by the oxidation of acrolein and the unreacted propylene. The other part of this diagram is similarly found in the process illustrated in FIG. 1. In this diagram, the reference numerals which are the sums of the reference numerals of FIG. 1 plus 100 denote the identical members shown in FIG. 1.

Though this invention has been described as embodied in the process for the production of acrylic acid by the partial oxidation of propylene has been described, it can be similarly embodied in the process for the production of acrylic acid by the partial oxidation of isobutylene.

For the purpose of producing (meth) acrylic acid by using the method for managing the operation mentioned above, by supplying propylene or isobutylene, t-butanol, or methyl-t-butyl ether together with a molecular oxygen-containing gas, optionally plus an inert gas to a reactor formed by combining a former stage reactor packed with a catalyst for forming acrolein or methacrolein by the oxidation of isobutylene, t-butanol, or methyl-t-butyl ether and a latter stage reactor packed with a catalyst for forming acrylic acid or methacrylic acid by the oxidation of acrolein or methacrolein and inducing the relevant components to react at a prescribed temperature, it is made possible to produce acrylic acid or methacrylic acid eventually.

For the purpose of producing acrylic acid by the reaction of two-stage catalytic gas phase oxidation of a propylene-containing gas according to this invention, the oxidizing catalyst which is generally used in producing acrolein by the reaction of gas phase oxidation of a raw material gas containing propylene can be adopted as the former-stage catalyst, for example. By the same token, as the latter-stage catalyst which does not need to be particularly discriminated, the oxidizing catalyst which is generally used in producing acrylic acid by the gas phase oxidation of a reaction gas obtained in the former stage of the method for two-stage catalytic gas phase oxidation and mainly containing acrolein can be adopted.

As typical examples of the former-stage catalyst, such catalysts which are represented by the general formula $Mo_a$—$Bi_b$—$Fe_c$-$A_d$-$B_e$-$C_f$-$D_g$-$O_x$ (wherein Mo, Bi, and Fe denote molybdenum, bismuth, and iron respectively, A denotes at least one element selected between nickel and cobalt, B denotes at least one element selected among alkali metals and thallium, C denotes at least one element selected from the group consisting of phosphorus, niobium, manganese, cerium, tellurium, tungsten, antimony, and lead, D denotes at least one element selected from the group consisting of silicon, aluminum, zirconium, and titanium, and O denotes oxygen, and a, b, c, d, e, f, g, and x denote the atomic ratios respectively of Mo, Bi, Fe, A, B, C, D and O such that b=0.1–1.0, c=0.1–10, d=2–20, e=0.001–5, f=0–5, and g=0–30 are satisfied when a=12 is fixed, and x denotes the value which is determined by the states of oxidation of the relevant elements) may be cited.

Then, as typical of the latter-stage catalyst, such catalysts which are represented by the general formula $Mo_a$—$V_b$—$W_c$—$Cu_d$-$A_e$-$B_f$-$C_g$—$O_x$ (wherein Mo denotes molybdenum, V denotes vanadium, W denotes tungsten, Cu denotes copper, A denotes at least one element selected among antimony, bismuth, tin, niobium, cobalt, iron, nickel and chromium, B denotes at least one element selected among alkali metal, alkaline earth metals, and thallium, C denotes at least one element selected among silicon, aluminum, zirconium, and cerium, and O denotes oxygen, and a, b, c, d, e, f, g, and x denote the atomic ratios respectively of Mo, V, W, Cu, A, B, C, and O such that b=2–14, c=0–12, d=0.1–5, e=0–5, f=0–5, and g=0–20 are satisfied when a=12 is fixed, and x denotes the value which is determined by the states of oxidation of the relevant elements) may be cited.

As the catalyst to be used in obtaining methacrylic by the reaction of two-stage catalytic gas phase oxidation of isobutylene, t-butanol, or methyl-t-butyl ether as contemplated by this invention, the oxidation catalyst which is generally used in producing methacrolein by the reaction of gas phase oxidation of a raw material gas containing isobutylene may be adopted as the former-stage catalyst, for example. By the same token, as the latter-stage catalyst which does not need to be particularly discriminated, the oxidation catalyst which is generally used in producing methacrylic acid by the gas phase oxidation of a reaction gas containing methacrolein mainly which is obtained by the former stage of the method of two-stage catalytic gas phase oxidation.

To be specific, among other former-stage catalysts defined above, those which are represented by the general formula $Mo_a$—$W_b$—$Bi_c$—$Fe_d$-$A_e$-$B_f$-$C_g$-$D_h$-$O_x$ (wherein Mo, W, an denote molybdenum, tungsten, and bismuth, Fe denotes iron, A denotes nickel and/or cobalt, B denotes at least one element selected among alkali metals, alkaline earth metals, and thallium, C denotes at least one element selected from the group consisting of phosphorus, tellurium, antimony, tin, cerium, lead, niobium, manganese, and zinc, D denotes at least one element selected from the group consisting of silicon, aluminum, titanium, and zirconium, and O denotes oxygen, and a, b, c, d, e, f, g, h, and x denote the numbers of atoms respectively of Mo, W, Bi, Fe, A, B, C, D, and O such that b=0–10, c=0.1–10, d=0.1–20, e=2–20, f=0.001–10, g=0–4, and h=0–30 are satisfied when a=12 is fixed, and x denotes the value determined by the states of oxidation of the relevant elements) prove particularly advantageous.

The latter-stage catalyst does not need to be particularly discriminated but is only required to be a catalyst of one or more oxides containing molybdenum and phosphorus as main components. For example, it is preferred to be a phosphomolybdic acid type heteropoly acid or a metal salt thereof. As typical examples of the catalyst answering this description, the catalysts represented by the general formula $Mo_a$—$P_b$-$A_c$-$B_d$-$C_e$-$D_f$-$O_x$ (wherein Mo denotes molybdenum, P denotes phosphorus, A denotes at least one element selected from the group consisting of arsenic, antimony, germanium, bismuth, zirconium, and selenium, B denotes at least one element selected from the group consisting of copper, iron, chromium, nickel, manganese, cobalt, tin, silver, zinc, palladium, rhodium, and tellurium, C denotes sat least one element selected from the group consisting of vanadium, tungsten, and niobium, D denotes at least one element selected from the group consisting of alkali metals, alkaline earth metals, and thallium, and O denotes oxygen, and a, b, c, d, e, f, and X denote the atomic ratios respectively of Mo, P, A, B, C, D, and O such that b=0.5–4, c=0–5, d=0–3, e=0–4, and f=0.01–4 are satisfied when a=12 is fixed, and x represents the value to be determined by the states of oxidation of the relevant elements) may be cited.

The catalyst does not need to be particularly discriminated on account of the shape thereof. It may be in the shape of spheres, cylinders, and circular columns, for example. As the method for molding the catalyst in such a shape, carrying molding, extrusion molding, and tablet molding may be adopted. Further, the catalyst which is formed by depositing such a catalytic substance as described above on a refractory carrier is also useful.

The conditions for effecting the reaction of gas phase catalytic oxidation of propylene or isobutylene with molecular oxygen may be adopted from those in popular use in the pertinent methods known to the art. In the case of using propylene, for example, the propylene concentration in the raw material gas is in the range of 3–15 volume %, the ratio of the molecular oxygen to the propylene is in the range of 1–3, and the remainder of the raw material gas comprises nitrogen, steam, carbon oxides, propane, etc.

Air is advantageously used as the source of supply of molecular oxygen. Optionally, oxygen-enriched air or pure oxygen may be used instead. The one-pass method or the recycling method may be employed for the use of the molecular oxygen in the reaction. Preferably, the reaction is carried out with the reaction temperature set in the range of 250° C.–450° C., the reaction pressure in the range from normal pressure to 500 kPa, and the space velocity in the range of 500–3000 $h^{-1}$ (STP).

Then, in the case of using isobutylene for the reaction of gas phase catalytic oxidation, the isobutylene concentration in the raw material gas is in the range of 1–10 volume %, the concentration of molecular oxygen relative to isobutylene is in the range of 3–20 volume %, the concentration of steam is in the range of 0–60 volume %, and the remainder of the raw material gas comprises nitrogen, carbon oxides, etc. Air is advantageously used as the source of supply of molecular oxygen. Optionally, oxygen-enriched air or pure oxygen may be used instead. Preferably, the reaction is carried out with the reaction temperature set in the range of 250° C.–450° C., the reaction pressure in the range from normal pressure to 500 kPa, and the space velocity in the range of 300–5000 $h^{-1}$ (STP).

Then, for the purpose of forming acrylic acid, the mixed gas formed by adding the acrolein-containing gas obtained by the aforementioned former-stage reaction and secondary air, secondary oxygen or steam as optional components together is supplied into a shell-and-tube exchanger type second reactor having the aforementioned oxide catalyst (latter-stage catalyst) fill the individual tubes of the tube bundle part inside the shell at a reaction temperature (heat medium temperature in the reactor ) in the range of 100°–380° C., preferably 150°–350° C., and a space velocity in the range of 300–5,000 $hr^{-1}$ (STP) so as to induce the latter-stage reaction and obtain acrylic acid.

Further, for the purpose of forming methacrylic acid, the mixed gas formed by adding the methacrolein-containing gas obtained by the aforementioned former-stage reaction and secondary air and secondary oxygen or steam as optional components together is supplied into a shell-and-tube exchanger type second reactor having the aforementioned oxide catalyst (latter-stage catalyst) fill the individual tubes of the tube bundle part inside the shell at a reaction temperature (heat medium temperature in the reactor ) in the range of 100°–380° C., preferably 150°–350° C., and a space velocity in the range of 300–5,000 $hr^{-1}$ (STP) so as to induce the latter-stage reaction and obtain methacrylic acid.

This invention can be applied to a reactor of the type partitioned with an intermediate tube sheet into two chambers, an upper one and a lower one.

Now, this invention will be more specifically described below by adducing working examples.

EXAMPLE 1

In a process for producing acrylic acid by the catalytic gas phase oxidation of propylene, comprising a step for forming acrolein by the oxidation of propylene and a step for forming acrylic acid by the oxidation of acrolein and using a single reactor 1 as illustrated in FIG. 1, the former stage region 2a of the reactor 1 was packed with a catalyst having the composition of $Mo_{12}Bi_{1.2}Fe_1Co_5Ni_1W_{0.5}Si_1K_{0.06}$ as the former-stage catalyst for the formation of acrolein and the latter stage region 2b of the reactor 1 was packed with a catalyst having the composition of $Mo_{12}V_{5.0}W_{1.0}Cu_{2.2}Sb_{0.2}$ as the latter-stage catalyst for the formation of acrylic acid.

Then, propylene as the raw material from the propylene supply source 3 was supplied through the flow meter 4 and the control valve 5 to the former stage side region 2a of the reactor 1 via the conduit 6. Air from the air supply source 8 was supplied through the control valve 9, the blower 10, and the flow meter 11 to the former stage side region 2a of the reactor 1 via the conduit 12.

The reaction product gas emanating from the latter stage side region 2b of the reactor 1 was introduced through the heat exchanger 14 into the lower part of the absorption column 15 via the conduit 13. The reaction product gas which had made counterflow contact in the absorption column 15 with the absorption liquor 20 supplied from above had such products as acrylic acid absorbed by the absorption liquor and was recovered as the collected liquor through the bottom of the column by means of the pump 16. Further, part of the collected liquor 17 was returned to the intermediate stage of the absorption column 15 through the control valve 18 and the heat exchanger 19. Such gases as the unreacted propylene and nitrogen gas were separated through the top of the column and recycled through the flow meter 22 and the control valve 2 to the reactor 1 via the conduit 21. The remained gases were discharged through the pressure gauge 24 and the control valve 25 via the conduit 26.

The measured value of propylene 3 indicated on the flow meter 4 was transmitted as a signal by the wiring 27 to the inlet gas concentration calculating device 28. The measured value of the air 8 indicated on the flow meter 11 was transmitted as a signal by the wiring 29 to the inlet gas concentration calculating device 28. The measured value of the recycling gas indicated on the flow meter 22 is also transmitted as a signal by the wiring 30 to the inlet gas concentration calculating device 28. Further, the measured value of the discharged gas indicated on the pressure gauge 24 was transmitted as a signal by the wiring 31 to the inlet gas concentration calculating device 28. The measured value of the temperature at the top of the absorption column 15 indicated on the thermometer 32 was transmitted as a signal by the wiring 33 to the control valve 18, wherein the amount of the liquor to be passed the heat exchanger 19 was controlled by regulating the degree of opening of the valve, and the measured value was transmitted as a signal by the wiring 34 to the inlet gas concentration calculating device 28.

Then, the propylene concentration and the oxygen concentration at the inlet port of the reactor 1 were automatically calculated with the inlet gas concentration calculating device 28, a process control device, on the basis of the material balance using the measured values of raw material propylene flow rate, air flow rate, column top temperature and column top pressure and the fixed input values 37 of air temperature and humidity, degree of propylene conversion, and propylene concentration by the use of various flow meters, thermometers, and pressure gauges mentioned above and the results of the automatic calculation were rated with the object of determining whether or not they fell in the ranges of the preset upper limits and lower limits of concentrations.

Meanwhile, the propylene concentration at the inlet port of the reactor 1 was analyzed with a gas concentration analyzing instrument 7 of the principle of gas chromatography. The measured value of this analysis was transmitted as a signal by the wiring 36 to the inlet gas concentration calculating device 28 with the object of rating this value and determining whether or not it fell in the range of the present upper limit and lower limit of the concentration. At this time, the apparatus mentioned above was operated under the following conditions.

| | |
|---|---|
| Flow rate of propylene | 25.3 m³ (standard condition)/minute |
| Flow rate of air | 213.7 m³ (standard condition)/minute |
| Flow rate of recycling gas | 119.1 m³ (standard condition)/minute |
| Temperature at top of absorption column | 61.9° C. |
| Pressure at top of absorption column | 11 kPa |

The fixed values used in the operation were as follows.

| | |
|---|---|
| Temperature of air | 31° C. |
| Humidity of air | 78% |
| Conversion of propylene | 97.5% |
| Purity of propylene | 98.0% |

For the ranges specified above, the following values were set.

| | |
|---|---|
| Upper limit of propylene concentration | 8.0 volume % |
| Lower limit of propylene concentration | 6.5 volume % |
| Upper limit of oxygen concentration | 14.6 volume % |
| Lower limit of oxygen concentration | 12.0 volume % |

The measured values obtained after the operation of the apparatus and the measured values of analysis were as follows.

| | |
|---|---|
| Calculated value of propylene concentration | 7.02 volume % |
| Measured value of propylene concentration | 6.98 volume % |
| Calculated value of oxygen concentration | 12.5 volume % |
| Measured value of oxygen concentration | 12.6 volume % |

The measured value of propylene indicated on the online analyzing instrument suddenly rose to 8.5 volume % after the operation continued for one month. When the propylene concentration was conformed by manual analysis, it was found to be 7.03 volume %. When the online analyzing instrument was checked, the sudden rise was found to be an erroneous indication of measured value due to the deterioration of the separating column by aging. The indication was normalized, however, when the separating column was replaced with a new supply. Since the calculated value was normal at this time, the process was not brought to emergency stop.

EXAMPLE 2

In a process performed by following the procedure of Example 1, the former stage reactor 101a for forming acrolein by the oxidation of propylene was packed with a catalyst having the composition of $MO_{12}Bi_{1.2}Fe_1Co_5Ni_1W_{0.5}So_1K_{0.06}$ and the latter stage reactor 101b for forming acrylic acid by the oxidation of acrolein was packed with a catalyst having the composition of $Mo_{12}V_{5.0}W_{1.0}Cu_{2.2}Sb_{0.2}$.

Then, the former stage reactor 101a was supplied with propylene as the raw material. Further, the former stage reactor 101a was supplied with the air from the air supply source 108. The reaction product in the former stage reactor 101a was supplied via the conduit 113a to the latter stage reactor 101b together with the air which was supplied thereto through the control valve 138 and the flow meter 139 via the conduit 140. The reaction product in the latter stage reactor 101b was supplied through the conduit 113b and the heat exchanger 114 to the absorption column 115. The other conditions of this process were similar to those of Example 1. The measured value indicated on the flow meter 139 was transmitted as a signal by the wiring 140 to the inlet gas concentration calculating device 128.

At this time, the apparatus was operated under the following conditions.

| | |
|---|---|
| Flow rate of propylene | 25.3 m³ (standard condition)/minute |
| Flow rate of air for first stage reactor | 137.3 m³ (standard condition)/minute |
| Flow rate of air for second stage reactor | 74.3 m³ (standard condition)/minute |
| Flow rate of recycling gas | 182.0 m³ (standard condition)/minute |
| Temperature at top of absorption column | 61.5° C. |
| Pressure at top of absorption column | 11 kPa |

The fixed values mentioned above were as follows.

| | |
|---|---|
| Temperature of air | 31° C. |
| Humidity of air | 78% |
| Degree of conversion of propylene | 97.5% |
| Purity of propylene | 98.0% |

For the ranges specified above, the following values were set

| | |
|---|---|
| Upper limit of propylene concentration | 8.0 volume % |
| Lower limit of propylene concentration | 6.5 volume % |
| Upper limit of oxygen concentration | 9.5 volume |
| Lower limit of oxygen concentration | 8.0 volume % |

The measured values after the operation of the apparatus and the measured values of analysis were as follows.

| | |
|---|---|
| Calculated value of propylene concentration | 7.29 volume % |
| Analyzed value of propylene concentration | 7.33 volume % |
| Calculated value of oxygen concentration | 8.8 volume % |

Analyzed value of oxygen concentration 8.8 volume %

Since the measured value of propylene indicated on the online analyzing instrument suddenly fell 0 volume % after the operation was continued for one month, the online analyzing instrument and the process control device were checked. The sudden fall was confirmed to have originated in the defect of a part for processing signal in the process control device. The indication was normalized by the replacement of the part with a new supply. Since the indication of the calculated value was normal, the process was not brought to emergency stop.

The entire disclosure of Japanese Patent Application No. 2003-070786 filed on Mar. 14, 2003 including specification, claims, drawings, and summary are incorporated herein by reference in its entirety.

What is claimed is:

1. A method for managing the operation of an apparatus for the reaction of gas phase oxidation while the apparatus is in trouble, comprising the step of stopping the operation of said apparatus exclusively when the value of the concentration of a gas obtained by calculation based on the flow rate of the gas at the inlet port of the relevant reactor and the value measured by analysis with a gas analyzing instrument both deviate from the relevant preset ranges.

2. A method according to claim 1, wherein said step of stopping of the operation comprises the steps of causing the concentration of a raw material gas and the concentration of oxygen at the inlet port of the reactor to be automatically calculated by an inlet gas concentration calculating device on the basis of the material balance using the measured values of flow rate, pressure and temperature at various points, and the fixed input values depending on the operation conditions and causing the consequently calculated concentrations to be rated with the object of determining whether or not they fall in the range between the upper limit values and the lower limit values of the preset concentrations.

3. A method according to claim 2, wherein the raw materials supplied to the reaction device are an unsaturated hydrocarbon and a molecular oxygen-containing gas.

4. A method according to claim 3, wherein said unsaturated hydrocarbon is an unsaturated hydrocarbon of 2–4 carbon atoms.

5. A method according to claim 3, wherein said unsaturated hydrocarbon is propylene or isobutylene.

6. A method for the production of (meth)acrylic acid by the gas phase oxidation of an unsaturated hydrocarbon with a molecular oxygen-containing gas in accordance with a method for managing the operation set forth in claim 1.

7. A method for the production of (meth)acrylic acid by the gas phase oxidation of an unsaturated hydrocarbon with a molecular oxygen-containing gas in accordance with a method for managing the operation set forth in claim 2.

* * * * *